US010251941B2

(12) United States Patent
Turecek et al.

(10) Patent No.: US 10,251,941 B2
(45) **Date of Patent: *Apr. 9, 2019**

(54) FACTOR VIIA-POLYSIALIC ACID CONJUGATES HAVING PROLONGED IN VIVO HALF-LIFE

(71) Applicants: BAXALTA INCORPORATED, Bannockburn, IL (US); BAXALTA GMBH, Glattpark (Opfikon) (CH)

(72) Inventors: Peter Turecek, Klosterneuburg (AT); Juergen Siekmann, Vienna (AT); Friedrich Scheiflinger, Vienna (AT); Michel Canavaggio, Vienna (AT)

(73) Assignees: Baxalta Incorporated, Bannockburn, IL (US); Baxalta GmbH, Zug (CH)

( * ) Notice: Subject to any disclaimer, the term of this patent is extended or adjusted under 35 U.S.C. 154(b) by 184 days.

This patent is subject to a terminal disclaimer.

(21) Appl. No.: 14/946,286

(22) Filed: Nov. 19, 2015

(65) Prior Publication Data

US 2016/0129121 A1 May 12, 2016

Related U.S. Application Data

(63) Continuation of application No. 14/136,328, filed on Dec. 20, 2013, now abandoned, which is a continuation of application No. 11/956,634, filed on Dec. 14, 2007, now Pat. No. 8,637,007.

(60) Provisional application No. 60/875,217, filed on Dec. 15, 2006.

(51) Int. Cl.

| | |
|---|---|
| ***A61K 38/48*** | (2006.01) |
| ***C12N 9/64*** | (2006.01) |
| ***C12N 9/96*** | (2006.01) |
| ***A61K 47/54*** | (2017.01) |
| ***A61K 47/61*** | (2017.01) |

(52) U.S. Cl.

CPC ........ *A61K 38/4846* (2013.01); *A61K 47/549* (2017.08); *A61K 47/61* (2017.08); *C12N 9/6437* (2013.01); *C12N 9/96* (2013.01); *C12Y 304/21021* (2013.01); *Y02A 50/463* (2018.01)

(58) Field of Classification Search

CPC .. A61K 38/4846; A61K 47/549; A61K 47/61; C12N 9/6437; C12N 9/96; C12Y 304/21021; Y02A 50/463

See application file for complete search history.

(56) References Cited

U.S. PATENT DOCUMENTS

| | | | | |
|---|---|---|---|---|
| 7,199,223 B2 * | 4/2007 | Bossard | A61K 38/37 | 530/350 |
| 2009/0227504 A1 * | 9/2009 | Klausen | A61K 38/4846 | 514/14.3 |
| 2010/0015684 A1 * | 1/2010 | DeFrees | C12N 9/6437 | 435/188 |
| 2010/0062973 A1 * | 3/2010 | Frank | A61K 47/61 | 514/11.4 |

OTHER PUBLICATIONS

Jurlander (20010 Seminars in Thrombosis and Hemostasis 27(4): 373-383 (Year: 2001).*

* cited by examiner

*Primary Examiner* — Lisa J Hobbs
(74) *Attorney, Agent, or Firm* — Morgn, Lewis & Bockius LLP

(57) ABSTRACT

The present invention relates to a proteinaceous construct comprising plasmatic or recombinant factor VIIa (FVIIa) or biologically active derivatives thereof, which are bound to a carbohydrate moiety comprising 1-4 sialic acid units, wherein the in vivo half-life of the proteinaceous construct is substantially prolonged in the blood of a mammal, as compared to the in vivo half-life of a FVIIa molecule not bound to a carbohydrate moiety. The invention also provides a method for controlling bleeding in a mammal having a bleeding disorder due to functional defects or deficiencies of FVIIa, FVIII, or FIX. The invention also provides a method for controlling bleeding in a mammal during surgery or trauma.

11 Claims, 8 Drawing Sheets

FACTOR VIIA-POLYSIALIC ACID CONJUGATES HAVING PROLONGED IN VIVO HALF-LIFE

CROSS-REFERENCE TO RELATED APPLICATION

This application claims priority to U.S. Provisional Application No. 60/875,217 filed Dec. 15, 2006.

FIELD OF THE INVENTION

The present invention relates to a proteinaceous construct comprising coagulation factor VIIa (FVIIa) being bound to a carbohydrate moiety comprising a chain of 1-4 sialic acid units. Further the present invention relates to methods for prolonging the in vivo-half-life of blood coagulation proteins, especially FVIIa in the blood of a mammal having a bleeding disorder associated with functional defects or deficiencies of at least FVIIa, factor VIII (FVIII), and factor IX (FIX).

BACKGROUND OF THE INVENTION

The blood coagulation cascade is divided into three distinct segments: the intrinsic, extrinsic, and common pathways (Schenone et al., Curr Opin Hematol. 2004; 11:272-7). The cascade involves a series of serine protease enzymes (zymogens) and protein cofactors. When required, an inactive zymogen precursor is converted into the active form, which consequently converts the next enzyme in the cascade.

The intrinsic pathway requires the clotting factors VIII, IX, X, XI, and XII. Initiation of the intrinsic pathway occurs when prekallikrein, high-molecular-weight kininogen, factor XI (FXI) and factor XII (FXII) are exposed to a negatively charged surface. Also required are calcium ions and phospholipids secreted from platelets.

The extrinsic pathway is initiated when the vascular lumen of blood vessels is damaged. The membrane glycoprotein tissue factor is exposed and then binds to circulating factor VII (FVII) and to small preexisting amounts of its activated form FVIIa. This binding facilitates full conversion of FVII to FVIIa and subsequently, in the presence of calcium and phospholipids, the conversion of factor IX (FIX) to factor IXa (FIXa) and factor X (FX) to factor Xa (FXa). The association of FVIIa with tissue factor enhances the proteolytic activity by bringing the binding sites of FVII for the substrate (FX and FIX) into closer proximity and by inducing a conformational change, which enhances the enzymatic activity of FVIIa. The rate of FX activation by the extrinsic pathway is approximately 50 times slower than the rate achieved by the (intrinsic) pathway of FIXa, FVIIIa, phospholipid, and calcium ions.

The activation of FX is the common point of the two pathways. Along with phospholipid and calcium, factors Va (FVa) and Xa convert prothrombin to thrombin (prothrombinase complex), which then cleaves fibrinogen to form fibrin monomers. The monomers polymerize to form fibrin strands. Factor XIIIa (FXIIIa) covalently bonds these strands to one another to form a rigid mesh.

Conversion of FVII to FVIIa is also catalyzed by a number of proteases, including thrombin, FIXa, FXa, factor XIa (FXIa), and factor XIIa (FXIIa). For inhibition of the early phase of the cascade, tissue factor pathway inhibitor targets FVIIa/tissue factor/FXa product complex.

FVII (also known as stable factor or proconvertin) is a vitamin K-dependent serine protease glycoprotein with a pivotal role in hemostasis and coagulation (Eigenbrot, Curr Protein Pept Sci. 2002; 3:287-99).

FVII is synthesized in the liver and secreted as a single-chain glycoprotein of 48 kD. FVIIa shares with all vitamin K-dependent serine protease glycoproteins a similar protein domain structure consisting of an amino-terminal gamma-carboxyglutamic acid (Gla) domain with 9-12 residues responsible for the interaction of the protein with lipid membranes, a carboxy-terminal serine protease domain (catalytic domain), and two epidermal growth factor-like domains containing a calcium ion binding site that mediates interaction with tissue factor.

Gamma-glutamyl carboxylase catalyzes carboxylation of Gla residues in the amino-terminal portion of the molecule. The carboxylase is dependent on a reduced form of vitamin K for its action, which is oxidized to the epoxide form. Vitamin K epoxide reductase is required to convert the epoxide form of vitamin K back to the reduced form.

The major proportion of FVII circulates in plasma in zymogen form, and activation of this form results in cleavage of the peptide bond between arginine 152 and isoleucine 153. The resulting activated FVIIa consists of a $NH_2$-derived light chain (20 kD) and a COOH terminal-derived heavy chain (30 kD) linked via a single disulfide bond (Cys 135 to Cys 262). The light chain contains the membrane-binding Gla domain, while the heavy chain contains the catalytic domain.

The plasma concentration of FVII determined by genetic and environmental factors is about 0.5 mg/mL (Pinotti et al., Blood. 2000; 95:3423-8). Different FVII genotypes can result in several-fold differences in mean FVII levels. Plasma FVII levels are elevated during pregnancy in healthy females and also increase with age and are higher in females and in persons with hypertriglyceridemia. FVII has the shortest half-life of all procoagulant factors (3-6 h). The mean plasma concentration of FVIIa is 3.6 ng/mL in healthy individuals and the circulating half-life of FVIIa is relatively long (2.5 h) compared with other coagulation factors.

Hereditary FVII deficiency is a rare autosomal recessive bleeding disorder with a prevalence estimated to be 1 case per 500,000 persons in the general population (Acharya et al., J Thromb Haemost. 2004; 2248-56). Acquired FVII deficiency from inhibitors is also very rare. Cases have also been reported with the deficiency occurring in association with drugs such as cephalosporins, penicillins, and oral anticoagulants. Furthermore, acquired FVII deficiency has been reported to occur spontaneously or with other conditions, such as myeloma, sepsis, aplastic anemia, with interleukin-2 and antithymocyte globulin therapy.

Replacement therapy is the mainstay of treatment for patients with FVII deficiency (Mariani et al., Semin Hematol. 2006; 43(Suppl 1):S42-7). This has traditionally been achieved using fresh frozen plasma (FFP), prothrombin complex concentrates (PCCs), or plasma-derived FVII concentrates. However, recombinant FVIIa (rFVIIa) is now widely used for therapy in these patients.

RFVIIa has also been developed for treatment of bleedings in hemophilia A and B patients with inhibitors, and has been found to induce hemostasis even during major surgery such as major orthopedic surgery (Hedner, J Biotechnol. 2006; 124:747-57). RFVIIa is being produced in BHK cell cultures and has been shown to be very similar to plasma-derived FVIIa. The use of rFVIIa in hemophilia treatment is based on the low affinity binding of FVIIa to the surface of thrombin activated platelets. By the administration of pharmacological doses of exogenous rFVIIa the thrombin generation on the platelet surface at the site of injury is enhanced independently of the presence of FVIII/FIX. As a result of the increased and rapid thrombin formation, a tight fibrin hemostatic plug is being formed.

Although originally developed for the treatment of FVII deficiency and inhibitor-complicated hemophilia A and B, novel indications for rFVIIa (based on case reports and smaller clinical trials) include use in patients with liver disease, thrombocytopenia, or qualitative platelet dysfunction and in patients with no coagulation disorders who are bleeding as a result of extensive surgery or major trauma.

Therapeutic polypeptide drugs such as blood coagulation protein including FVIIa are rapidly degraded by proteolytic enzymes and neutralized by antibodies. This reduces their half-life and circulation time, thereby limiting their therapeutic effectiveness. Relatively high doses and frequent administration are necessary to reach and sustain the desired therapeutic or prophylactic effect of FVIIa. As a consequence adequate dose regulation is difficult to obtain and the need of frequent intravenous administrations imposes restrictions on the patient's way of living. Thus an improved FVIIa molecule with a longer circulation half-life would decrease the number of necessary administrations.

In principal, there are four general options for half-life extension of proteins in the blood circulation:

Direct chemical or enzymatic modification

Use of carrier molecules to protect the proteins in the circulation

Construction of mutants to extent half-life

Modification of the degradation pathway.

The present invention teaches an improvement of blood coagulation proteins, especially the FVIIa molecule by chemical modification. For chemical modification of therapeutic polypeptides several approaches have been used in the past.

PEGylation of polypeptide drugs protects them and improves their pharmacodynamic and pharmacokinetic profiles (Harris and Chess, Nat Rev Drug Discov. 2003; 2:214-21). The PEGylation process attaches repeating units of polyethylene glycol (PEG) to a polypeptide drug. PEG molecules have a large hydrodynamic volume (5-10 times the size of globular proteins), are highly water soluble and hydrated, very mobile, non-toxic, non-immunogenic and rapidly cleared from the body. PEGylation of molecules can lead to increased resistance of drugs to enzymatic degradation, increased half-life in vivo, reduced dosing frequency, decreased immunogenicity, increased physical and thermal stability, increased solubility, increased liquid stability, and reduced aggregation. The first PEGylated drugs were approved by the FDA in the early 1990s. In the meantime the FDA approved several PEGylated drugs for oral, injectable, and topical administration.

GlycoPEGylation™ technology includes methods that provide a peptide conjugate between a PEG polymer and a peptide, with the PEG covalently attached to the peptide via an intact glycosyl-linking group.

Liposomes have been used to encapsulate a variety of molecules such as DNA, anti-sense RNA, antibiotics, anticancer, and anti-fungal drugs, inhibitors/activators, antibodies (immunoliposomes), and antigens (for vaccines).

Phospholipids can be also conjugated to PEGs (PEG-liposome) for example via an amide linkage, carboxy-PEG and purified soy phosphatidylethanolamine (PE), esters and carbamate derivatives, the carbamate derivative being the most widely used today (U.S. Pat. No. 6,593,294). The molecular weights of the most commonly used PEG's are 2,000 and 5,000, but PEG's ranging from 600 to 12,000 are also used.

Acidic monosaccharide-substituted proteins were first disclosed in U.S. Pat. No. 3,847,890. In this patent acidic monosaccharides, i.e. n-acetylneuraminic acid and gluconate were substituted onto $\alpha$-amino or $\varepsilon$-amino groups of insulin, human growth hormone or albumin to reduce the antigenicity of the polypeptides.

Polysialic acid (PSA), also referred as colominic acid (CA), is a naturally occurring polysaccharide. It is a homopolymer of N-acetylneuraminic acid with $\alpha(2\rightarrow 8)$ ketosidic linkage and contains vicinal diol groups at its non-reducing end. It is negatively charged and a natural constituent of the human body. It can easily be produced from bacteria in large quantities and with pre-determined physical characteristics (U.S. Pat. No. 5,846,951). Being chemically and immunologically identical to polysialic acid in the human body, bacterial polysialic acid is non-immunogenic, even when coupled to proteins. Unlike other polymers (eg. PEG), polysialic acid is biodegradable. Covalent coupling of colominic acid to catalase and asparaginase led to an increase of enzyme stability in the presence of proteolytic enzymes or blood plasma. Comparative studies in vivo with polysialylated and unmodified asparaginase revealed that polysialylation increased the half-life of the enzyme (Fernandes and Gregoriadis, Int J Pharm. 2001; 217:215-24)

However, to date no therapeutic compounds consisting of a polypeptide conjugated to an acidic monosaccharide as described in U.S. Pat. No. 3,847,890 are commercially available. In contrast, U.S. Pat. No. 5,846,951 teaches that the polysaccharide portion of the compound should have at least 5, and in other embodiments at least 20 or 50 sialic acid residues in the polymer chain. Because the polysaccharides are usually produced in bacteria carrying the inherent risk of copurifying endotoxins, the purification of long sialic acid polymer chains may raise the probability of increased endotoxin content. Short PSA molecules with a 1-4 sialic acid units can also be synthetically prepared (Kang et al., Chem Commun. 2000; 227-8; Ress and Linhardt, Current Organic Synthesis. 2004; 1:31-46), thus minimizing the risk of high endotoxin levels.

WO 98/32466A1 suggests that FVII, among many other proteins, may be PEGylated but does not contain any working examples supporting the disclosure.

WO 01/58935A3 teaches conjugates comprising at least one non-polypeptide moiety covalently attached to a polypeptide, wherein the amino acid sequence of the polypeptide differs from that of wild-type FVII or FVIIa in that at least one amino acid residue comprising an attachment group for said non-polypeptide moiety has been introduced or removed. For the non-polypeptide moieties especially PEG was suggested.

US20050113565A1 discloses a FVII polypeptide or FVII-related polypeptide, wherein the polypeptide comprises one or more asparagine-linked and/or serine-linked oligosaccharide chains, and wherein at least one of said oligosaccharide groups is covalently attached to at least one polymeric group (PEG, "glycoPEGylation").

Thus, there remains a need in the art for compositions and methods that provide clotting protein preparations comprising improved plasma derived or rFVII, modified FVII, or FVII-related polypeptide.

SUMMARY OF THE INVENTION

The present invention provides a proteinaceous construct comprising plasmatic or recombinant factor VIIa (FVIIa) or biologically active derivatives thereof, said FVIIa or said biologically active derivatives thereof being bound to a chain of 1-4 sialic acid units, wherein the in vivo-half-life of the proteinaceous construct is substantially prolonged in the blood of a mammal, particularly a human, compared to FVIIa or derivatives thereof lacking a chain of 1-4 sialic acid units. Additionally, pharmaceutical compositions containing said proteinaceous construct as well as methods for prolonging the in vivo-half-life of FVIIa in the blood of a mammal having a bleeding disorder associated with functional defects or deficiencies of at least one of FVIIa, FVIII and FIX using said proteinaceous construct are provided according to the present invention. The proteinaceous construct of the invention can also be administered to control bleeding in case of trauma or surgery in a mammal with normal levels of coagulation factors.

In one embodiment of the invention, a proteinaceous construct is provided comprising (a) an activated factor VII (FVIIa) molecule selected from the group consisting of plasmatic FVIIa, recombinant FVIIa (rFVIIa), and a biologically active derivative of FVIIa; and (b) at least one physiologically acceptable carbohydrate moiety comprising 1-4 sialic acid units bound to said FVIIa molecule; wherein the in vivo half-life of said construct is prolonged in the blood of a mammal as compared to the in vivo half-life of a FVIIa molecule that is not bound to said carbohydrate moiety.

In another embodiment of the invention, the aforementioned proteinaceous construct is provided wherein the in vivo half-life of said construct is increased by at least a factor of about two as compared to the in vivo half-life of a FVIIa molecule that is not bound to said carbohydrate moiety. In another embodiment, the aforementioned proteinaceous construct is provided wherein the in vivo half-life of said construct is increased by at least a factor of about three as compared to the in vivo half-life of a FVIIa molecule that is not bound to said carbohydrate moiety. In still another embodiment, the aforementioned proteinaceous construct is provided wherein the physiologically acceptable carbohydrate moiety is directly covalently linked to at least one amino acid residue of said FVIIa molecule.

In yet another embodiment of the invention, the aforementioned proteinaceous construct is provided wherein the physiologically acceptable carbohydrate moiety is non-covalently linked to at least one amino acid residue of said FVIIa molecule. In still another embodiment, the aforementioned proteinaceous construct is provided wherein said physiologically acceptable carbohydrate moiety is a polysialic acid or a derivative thereof.

In one embodiment of the invention, a pharmaceutical composition is provided comprising an effective amount of the aforementioned proteinaceous construct and one or more compounds selected from the group consisting of a pharmaceutically acceptable carrier, diluent, salt, buffer, and excipient.

In another embodiment of the invention, a method of controlling bleeding in a mammal having a bleeding disorder associated with functional defects or deficiencies of at least one of FVIIa, FVIII and FIX is provided comprising administering the aforementioned proteinaceous construct. In yet another embodiment, a method of controlling bleeding in a mammal during surgery or trauma is provided comprising administering the aforementioned proteinaceous construct.

In still another embodiment of the invention, a kit is provided comprising an effective amount of the aforementioned proteinaceous construct, packaged in a container, wherein the kit optionally contains a second therapeutic agent, and further comprising a label attached to or packaged with the container, the label describing the contents of the container and providing indications and/or instructions regarding use of the contents of the container for controlling bleeding in a mammal. In yet another embodiment, the aforementioned kit is provided wherein the container is a vial or bottle or prefilled syringe.

DETAILED DESCRIPTION OF THE INVENTION

It is to be understood that this invention is not limited to the FVII moieties described herein. It is one aspect of the present invention that relates to a proteinaceous construct comprising one member of the blood coagulation cascade, plasmatic (i.e., plasma-derived) and/or recombinant FVIIa or biologically active derivatives thereof (in the following also designated as "PSA-FVIIa-conjugate"), said FVII or said biologically active derivatives thereof being bound to one to four sialic acid moieties, wherein the in vivo-half-life of said FVIIa or said biologically active derivatives thereof is prolonged in the blood of a mammal. As used herein, the term "proteinaceous construct" refers to an activated factor VII (FVIIa) molecule selected from the group consisting of plasmatic FVIIa, recombinant FVIIa (rFVIIa), and a biologically active derivative of FVIIa; and (b) at least one physiologically acceptable carbohydrate moiety comprising 1-4 sialic acid units bound to said FVIIa molecule. As used herein, the term "plasmatic" refers to "plasma derived."

FVIIa Polypeptides and Polynucleotides

The FVIIa molecules useful for the present invention include the full-length protein, precursors of the protein, biologically active or functional subunits or fragments of the protein, and functional derivatives thereof. Reference to FVIIa is meant to include all potential forms of such proteins.

According to the present invention, the term "recombinant Factor VIIa" (rFVIIa) does not underlie a specific restriction and may include any rFVIIa, heterologous or naturally occurring, obtained via recombinant DNA technology, or a biologically active derivative thereof. In certain embodiments, the term encompasses proteins and nucleic acids, e.g., gene, pre-mRNA, mRNA, and polypeptides, polymorphic variants, alleles, mutants, and interspecies homologs that: (1) have an amino acid sequence that has greater than about 60% amino acid sequence identity, 65%, 70%, 75%, 80%, 85%, 90%, 91%, 92%, 93%, 94%, 95%, 96%, 97%, 98% or 99% or greater amino acid sequence identity, over a region of at least about 25, 50, 100, 200, 300, 400, or more amino acids (up to the full length sequence of 406 amino acids for the mature protein), to a polypeptide encoded by a referenced nucleic acid or an amino acid sequence described herein; (2) specifically bind to antibodies, e.g., polyclonal antibodies, raised against an immunogen comprising a referenced amino acid sequence as described herein immunogenic fragments thereof, and conservatively modified variants thereof; (3) specifically hybridize under stringent hybridization conditions to a nucleic acid encoding a referenced amino acid sequence as described herein, and conservatively modified variants thereof; (4) have a nucleic acid sequence that has greater than about 95%, greater than about 96%, 97%, 98%, 99%, or higher nucleotide sequence identity, over a region of at least about 25, 50, 100, 150, 200, 250, 500, 1000, or more nucleotides (up to the full length sequence of 1218 nucleotides of the mature protein), to a reference nucleic acid sequence as described herein.

As used herein, "endogenous FVIIa" includes FVIIa which originates from said mammal. It also includes FVIIa transcribed from a transgene or any other foreign DNA present in said mammal. As used herein, "exogenous FVIIa" includes FVIIa which does not originate from said mammal.

Variant (or analog) polypeptides include insertion variants, wherein one or more amino acid residues supplement an FVIIa amino acid sequence. Insertions may be located at either or both termini of the protein, or may be positioned within internal regions of the FVIIa amino acid sequence. Insertion variants, with additional residues at either or both termini, can include for example, fusion proteins and proteins including amino acid tags or labels. For example, the FVIIa molecule may optionally contain an N-terminal Met, especially when the molecule is expressed recombinantly in a bacterial cell such as *E. coli.*

In deletion variants, one or more amino acid residues in a FVIIa polypeptide are removed. Deletions can be effected at one or both termini of the FVIIa polypeptide, or with removal of one or more residues within the FVIIa amino acid sequence. Deletion variants, therefore, include all fragments of a FVIIa polypeptide sequence.

In substitution variants, one or more amino acid residues of a FVIIa polypeptide are removed and replaced with alternative residues. In one aspect, the substitutions are conservative in nature and conservative substitutions of this type are well known in the art. Alternatively, the invention embraces substitutions that are also non-conservative. Exemplary conservative substitutions are described in Lehninger, [Biochemistry, 2nd Edition; Worth Publishers, Inc., New York (1975), pp. 71-77] and set out immediately below.

Conservative Substitutions

| SIDE CHAIN CHARACTERISTIC | AMINO ACID |
|---|---|
| Non-polar (hydrophobic): | |
| A. Aliphatic | A L I V P |
| B. Aromatic | F W |
| C. Sulfur-containing | M |
| D. Borderline | G |
| Uncharged-polar: | |
| A. Hydroxyl | S T Y |
| B. Amides | N Q |
| C. Sulfhydryl | C |
| D. Borderline | G |
| Positively charged (basic) | K R H |
| Negatively charged (acidic) | D E |

Alternatively, exemplary conservative substitutions are set out immediately below.

Conservative Substitutions II

| ORIGINAL RESIDUE | EXEMPLARY SUBSTITUTION |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |

-continued

| ORIGINAL RESIDUE | EXEMPLARY SUBSTITUTION |
|---|---|
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention can be recombinant molecules (e.g., heterologous and encoding the wild type sequence or a variant thereof, or non-naturally occurring). Reference polynucleotide and polypeptide sequences include, e.g., GenBank Accession Nos. J02933 for the genomic sequence, M13232 for the cDNA (Hagen et al. PNAS 1986; 83: 2412-6), and P08709 for the polypeptide sequence (references incorporated herein in their entireties). A variety of polymorphisms of FVII have been described, for example see Sabater-Lleal et al. (Hum Genet. 2006; 118:741-51) (reference incorporated herein in its entirety).

As used herein "biologically active derivative" or "biologically active variant" includes any derivative or variant of a molecule having substantially the same functional and/or biological properties of said molecule, such as binding properties, and/or the same structural basis, such as a peptidic backbone or a basic polymeric unit.

As used herein, "plasma-derived FVIIa" or "plasmatic" includes all forms of the protein found in blood obtained from a mammal having the property of activating the coagulation pathway.

As used herein, "recombinant FVIIa" includes rFVIIa obtained via recombinant DNA technology. It may be produced by any method known in the art. One specific example is disclosed in U.S. Pat. No. 4,784,950. An example of such rFVIIa is NovoSeven manufactured and sold by Novo Nordisk.

FVIIa Production and Expression

The production of rFVIIa may include any method known in the art for (i) the production of recombinant DNA by genetic engineering, e.g. via reverse transcription of RNA and/or amplification of DNA, (ii) introducing recombinant DNA into procaryotic or eucaryotic cells by transfection, e.g. via electroporation or microinjection, (iii) cultivating said transformed cells, e.g. in a continuous or batchwise manner, (iv) expressing rFVIIa, e.g. constitutively or upon induction, and (v) isolating said FVIIa, e.g. from the culture medium or by harvesting the transformed cells, in order to (vi) obtain purified rFVIIa, e.g. via anion exchange chromatography or affinity chromatography.

The rFVIIa can be produced by expression in a suitable prokaryotic or eukaryotic host system characterized by producing a pharmacologically acceptable rFVIIa molecule. Examples of eukaryotic cells are mammalian cells, such as CHO, COS, HEK 293, BHK, SK-Hep, and HepG2. There is no particular limitation to the reagents or conditions used for producing or isolating rFVIIa according to the present invention and any system known in the art or commercially available can be employed.

A wide variety of vectors can be used for the preparation of the rFVIIa and can be selected from eukaryotic and prokaryotic expression vectors. Examples of vectors for prokaryotic expression include plasmids such as pRSET, pET, pBAD, etc., wherein the promoters used in prokaryotic expression vectors include lac, trc, trp, recA, araBAD, etc. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

Sialic Acid

As used herein, "sialic acid moieties" includes sialic acid monomers or polymers which are soluble in an aqueous solution or suspension and have no negative impact, such as side effects, to mammals upon administration of the PSA-FVIIa-conjugate in a pharmaceutically effective amount. There is no particular limitation to the sialic acid unit used according to the present invention. The polymers are characterized, in one aspect, as having from 1 to 4 units. Different sialic acids units can be also combined in a chain.

Sialic acid moieties can be bound to FVIIa for example by the method described in U.S. Pat. No. 4,356,170, which is herein incorporated by reference. In one embodiment of the invention the polysaccharide compound may be a naturally occurring polysaccharide, a derivative of a naturally occurring polysaccharide, or a naturally occurring polysaccharide derivative. Generally, all of the saccharide residues in the compound are sialic acid residues.

Other techniques for coupling PSA to polypeptides are also known. For example, US Publication No. 2007/0282096 describes conjugating an amine or hydrazide derivative of, e.g., PSA, to proteins. In addition, US Publication No. 2007/0191597 describes PSA derivatives containing an aldehyde group for reaction with substrates (e.g., proteins) at the reducing terminal end.

In one embodiment of the invention, the polysialic acid portion of the polysaccharide compound is highly hydrophilic, and in another embodiment the entire compound is highly hydrophilic. Hydrophilicity is conferred primarily by the pendant carboxyl groups of the sialic acid units, as well as the hydroxyl groups. The saccharide unit may contain other functional groups, such as, amine, hydroxyl or sulphate groups, or combinations thereof. These groups may be present on naturally occurring saccharide compounds, or introduced into derivative polysaccharide compounds.

Polysaccharide compounds of particular use for the invention are those produced by bacteria. Some of these naturally occurring polysaccharides are known as glycolipids. It is particularly advantageous if the polysaccharide compounds are substantially free of terminal galactose units, which tend to be recognized by galactose receptors of hepatocytes and Kupffer cells.

Linkage

FVIIa may be covalently linked to the polysaccharide compounds by any of various techniques known to those of skill in the art. Various examples are identified at column 7, line 15, through column 8, line 5 of U.S. Pat. No. 5,846,951.

Examples include linkage through the peptide bond between a carboxyl group on one of either the FVIIa or polysaccharide and an amine group of the other, or an ester linkage between a carboxyl group of one and a hydroxyl group of the other. Another linkage by which the active ingredient, e.g., FVIIa, could be covalently bonded to the polysaccharide compound is via a Schiff base, between a free amino group on the active ingredient being reacted with an aldehyde group formed at the non-reducing end of the polymer by periodate oxidation (Jennings and Lugowski, J Immunol. 1981; 127:1011-8; Fernandes and Gregoriadis, Biochim Biophys Acta. 1997; 1341;26-34). The generated Schiff Base can be stabilized by specific reduction with $NaCNBH_3$ to form a secondary amine. An alternative approach is the generation of terminal free amino groups in the polysialic acid (PSA) by reductive amination with $NH_4Cl$ after prior oxidation. Bifunctional reagents can be used for linking two amino or two hydroxyl groups. For example PSA containing an amino group can be coupled to amino groups of the protein with reagents like $BS^3$ (Bis(sulfosuccinimidyl)suberate/Pierce, Rockford, Ill.). In addition heterobifunctional cross linking reagents like Sulfo-EMCS (N-ε-Maleimidocaproyloxy)sulfosuccinimide ester/Pierce) can be used for instance to link amine and thiol groups.

In another approach, a PSA hydrazide can be prepared and coupled to the carbohydrate moiety of the protein after prior oxidation and generation of aldehyde functions.

A free amine group of the therapeutic protein may be reacted with the 1-carboxyl group of the sialic acid residue to form a peptidyl bond or an ester linkage can be formed between the 1-carboxylic acid group and a hydroxyl or other suitable active group on an active ingredient. Alternatively, a carboxyl group may form a peptide linkage with deacetylated 5-amino group. An aldehyde group of a molecule of a pharmaceutically active compound may form a Schiff base with the N-deacetylated 5-amino group of a sialic acid residue.

Alternatively, the polysaccharide compound may be associated in a non-covalent manner with the pharmaceutically active compound, e.g., FVIIa. For example the polysaccharide compound and the pharmaceutically active compound may be linked via hydrophobic interactions, for example via lipid components of the polysaccharide compound with a hydrophobic pharmaceutically active compound. Other non-covalent associations may be via electrostatic interactions, with oppositely charged ions attracting each other.

The pharmaceutically active compound may be directly covalently linked to the polysaccharide compound in stoichiometric amounts (e.g., 1:1). Alternatively, two or more molecules of polysaccharide compound may be linked to one molecule of active ingredient.

Use

The present invention is directed to increasing in vivo half-life of blood coagulation proteins, especially FVIIa or biologically active derivatives thereof having a bleeding disorder associated with functional defects or deficiencies of FVIIa as compared to the in vivo half-life of FVIIa not linked to at least one physiologically acceptable sialic acid moiety. The PSA-FVIIa-conjugate of the present invention can further be used for the treatment of bleeding disorders associated with functional defects or congenital or acquired deficiencies of at least one of FVIII and FIX.

According to the state of the art in therapy and according to international guidelines and regulations, the pharmacokinetics of infused FVIIa are recognized and accepted as valid surrogate markers for efficacy (Björkman and Berntrop, Clin Pharmacokinet. 2001; 40:815-32).

This is based on the validated assumption that an infused FVIIa product which had been characterized by standardized tests for functional activity will be found in the blood stream and will act there as expected as a component of the coagulation cascade. Therefore any pharmacokinetic analysis in animal models will be predictive for efficacy expected in patients treated with FVIIa products.

Half-Life

In one embodiment of the present invention, the in vivo half-life of the proteinaceous construct is prolonged. In a related embodiment, the in vivo half-life of the proteinaceous construct is prolonged by at least a factor of two, while in another embodiment the in vivo half-life is prolonged by at least a factor of three, as compared to FVIIa which is not bound to sialic acid. The prolonging of FVIIa half-life can be assessed by measuring the pharmacokinetics in rats, as described in the examples below.

Administration

The route of administration does not exhibit particular limitations, and in one embodiment the proteinaceous construct of the present invention may be administered by injection, such as intravenous, intramuscular, or intraperitoneal injection.

To administer compositions comprising a proteinaceous construct of the present invention to human or test animals, in one aspect, the compositions comprise one or more pharmaceutically acceptable carriers. The terms “pharmaceutically” or “pharmacologically acceptable” refer to molecular entities and compositions that are stable, inhibit protein degradation such as aggregation and cleavage products, and in addition do not produce allergic, or other adverse reactions when administered using routes well-known in the art, as described below. “Pharmaceutically acceptable carriers” include any and all clinically useful solvents, dispersion media, coatings, antibacterial and antifungal agents, isotonic and absorption delaying agents and the like, including those agents disclosed above.

As used herein, “effective amount” includes a dose suitable for treating a mammal having a bleeding disorder as outlined above.

The compositions may be administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

Single or multiple administrations of the compositions can be carried out with the dose levels and pattern being selected by the treating physician. For the prevention or treatment of disease, the appropriate dosage will depend on the type of disease to be treated, as described above, the severity and course of the disease, whether drug is administered for preventive or therapeutic purposes, previous therapy, the patient’s clinical history and response to the drug, and the discretion of the attending physician.

Pharmaceutical Compositions

The present invention also relates to a pharmaceutical composition comprising an effective amount of a proteinaceous construct as defined above. The pharmaceutical composition may further comprise a pharmaceutically acceptable carrier, diluent, salt, buffer, or excipient. The pharmaceutical composition can be used for treating the above-defined bleeding disorders. The pharmaceutical composition of the invention may be a solution or a lyophilized product. There are many known methods of forming stable solutions of proteins, and specifically FVIIa. One example is disclosed in U.S. Pat. No. 5,874,408. Solutions of the pharmaceutical composition may be subjected to any suitable lyophylization process.

Kits

As an additional aspect, the invention includes kits which comprise a composition of the invention packaged in a manner which facilitates its use for administration to subjects. In one embodiment, such a kit includes a compound or composition described herein (e.g., a composition comprising a proteinaceous construct), packaged in a container such as a sealed bottle or vessel, with a label affixed to the container or included in the package that describes use of the compound or composition in practicing the method. In one embodiment, the kit contains a first container having a composition comprising a proteinaceous construct and a second container having a physiologically acceptable reconstitution solution for the composition in the first container. In one aspect, the compound or composition is packaged in a unit dosage form. The kit may further include a device suitable for administering the composition according to a specific route of administration. Preferably, the kit contains a label that describes use of the therapeutic protein or peptide composition.

EXAMPLES

Example 1

Figure 1:
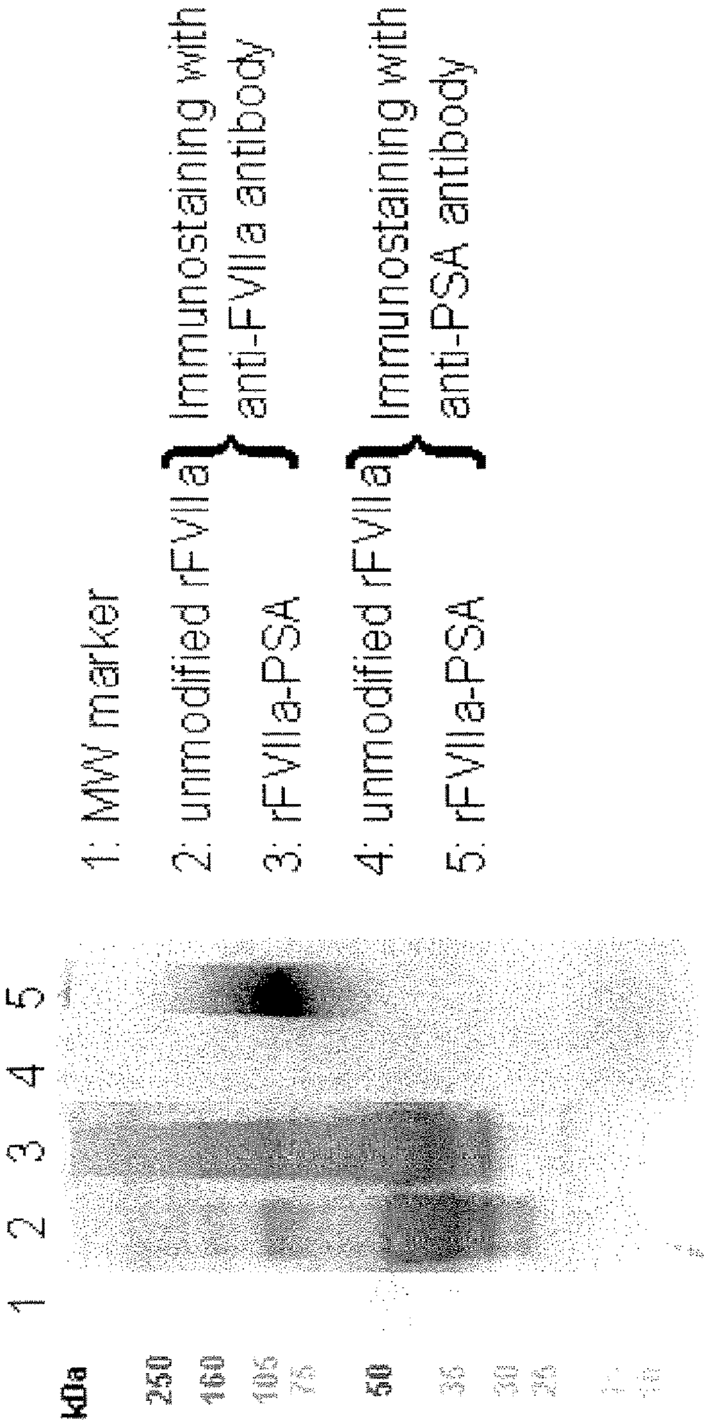
FIG. 1 shows a SDS-PAGE of rFVIIa after conjugation with PSA

Modification of Lysine Residues in rFVIIa with Colominic Acid

The modification of lysine residues with sialic acid (colominic acid, CA) was carried out as described by Jennings and Lugowski (J Immunol. 1981; 127;1011-8). For this procedure CA from Sigma (Sigma-Aldrich, St. Louis; Mo.) was used. An aqueous solution of CA (concentration: 20 mg/mL) containing 0.1 M $NaIO_4$ was stirred for 15 min in the dark at room temperature to oxidize the CA. Two mL ethylene glycol per mL of the activated CA solution was added and stirred for further 30 min in the dark at room temperature. The solution was dialyzed over night against 0.05 M sodium phosphate buffer, pH 7.2 in the dark at a temperature ranging from 2-8° C.

Subsequently an aliquot of this solution was added to a rFVIIa solution (30 μg/mL) in 0.05 M sodium phosphate buffer, pH 7.2 to give a final concentration of 100 mg activated CA per mg rFVIIa. This mixture was stirred for 180 min at room temperature in the dark. $NaCNBH_3$ was added (final concentration 10 mg/mg rFVIIa) and the mixture was incubated for 18 h at room temperature in the dark under gentle shaking. Then 2.5 mL of an aqueous 1 M TRIS-solution, pH 7.2 was added per mL of this mixture and stirred for 60 min to terminate the reaction.

The free reagents were separated from the rFVIIa-CA acid conjugate by ion exchange chromatography using a QHyperD F 50 μm resin (Pall BioSepra, Cergy, France) and a Pharmacia XK-10 column (Pharmacia XK 10; h=15 cm). The CA conjugated protein was eluted with elution buffer (20 mM HEPES/1 M NaCl, pH 8.0). In a final step the eluate was concentrated by ultrafiltration/diafiltration (UF/DF) using a 30 kD membrane (regenerated cellulose/Millipore) against 20 mM HEPES buffer, pH 7.4 containing 150 mM NaCl and 0.5% sucrose.

Example 2

Biochemical Characterization of Polysialylated rFVIIa

The enzymatic activity of rFVIIa-PSA was determined by a clotting assay, where FVIIa was added to a human FVII-deficient plasma and the clotting was triggered by a truncated tissue factor reacting with FVIIa but not with FVII (Staclot, Diagnostica Stago, Asnières, France).

The FVIII-bypassing activity of rFVII-PSA was measured by a thrombin generation assay (TGA), where FVIIa was added to a severe haemophilia A plasma, containing a high titer of anti-FVIII inhibitor in the presence of a thrombin-specific fluorescence peptide-substrate. Coagulation was triggered with a tissue factor-phospholipid complex and thrombin generation was continuously measured by the cleavage rate of the fluorophore of the substrate. The thrombin generation activity was calculated from the peak thrombin, i.e. the maximum thrombin concentration observed during the assay. In both cases a NovoSeven recombinant FVIIa preparation (Novo Nordisk, Copenhagen, Denmark) was used as reference.

As seen in Table 1 the specific activity of PSA-rFVIIa decreased after the modification.

TABLE 1

Specific activity of rFVIIa before and after conjugation with PSA

| | FVIIa activity | |
|---|---|---|
| | STF (U/mg protein) | TGA (U/mg protein) |
| unmodified rFVIIa | 45942 | 44296 |
| rFVIIa-PSA | 1003 | 22 |

Modification was visualized by SDS-PAGE performed under non-reducing conditions. Immunostaining was done with a polyclonal anti-FVII antibody (Affinity Biologicals; Ancaster, Canada) and with a monoclonal anti-PSA antibody (Chemicon International, Temecula, Calif., USA). Modification resulted in an increase of the MW of FVIIa demonstrated by a smeared area correlating with the PSA-containing protein (FIG. 1).

Example 3

Pharmacokinetic of rFVIIa-PSA-conjugate in Rats

Four rats (Crl:CD(SD), Charles River Laboratories, Wilmington, Mass.) were anaesthetized and rFVIIa-PSA-conjugate (16.500 U FVIIa/kg) in buffer (1.3 g/L glycylglycine, 3 g/L sodium chloride, 30 g/L mannitol, 1.5 g/L $CaCl_2 \times 2H_2O$, 0.1 g/L Tween 80, pH 5.5) was applied by intravenous injection into the tail vein in a volume dose of 20 mL per kg. Unmodified rFVIIa in a dose of 18.000 U FVIIa/kg was used as control in 6 normal rats. Blood samples were taken from retrobulbary venous plexus 5 min, 30 min, 1 h, 2, 4, 6, 8 and 24 h after substance application, citrate plasma was prepared and frozen for further analysis.

Figure 2:
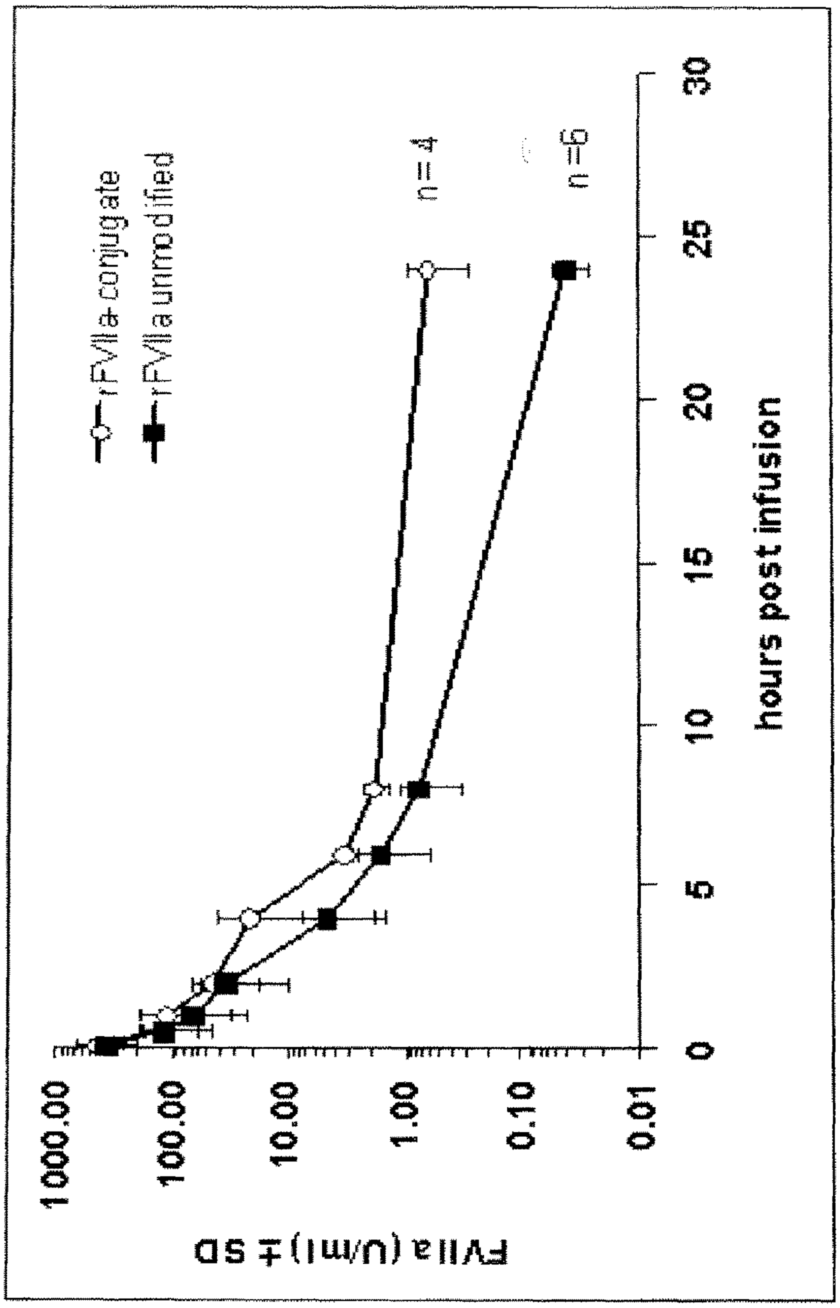
FIG. 2 shows the pharmacokinetics of rFVIIa-PSA-conjugate and unmodified rFVIIa in rats

Then the FVIIa activity (Staclot, Diagnostica Stago, Asnières, France) in plasma was measured. Half life of unmodified rFVIIa was 1.1 h and was increased to 2.3 h with the rFVIIa-conjugate (FIG. 2).

Figure 3:
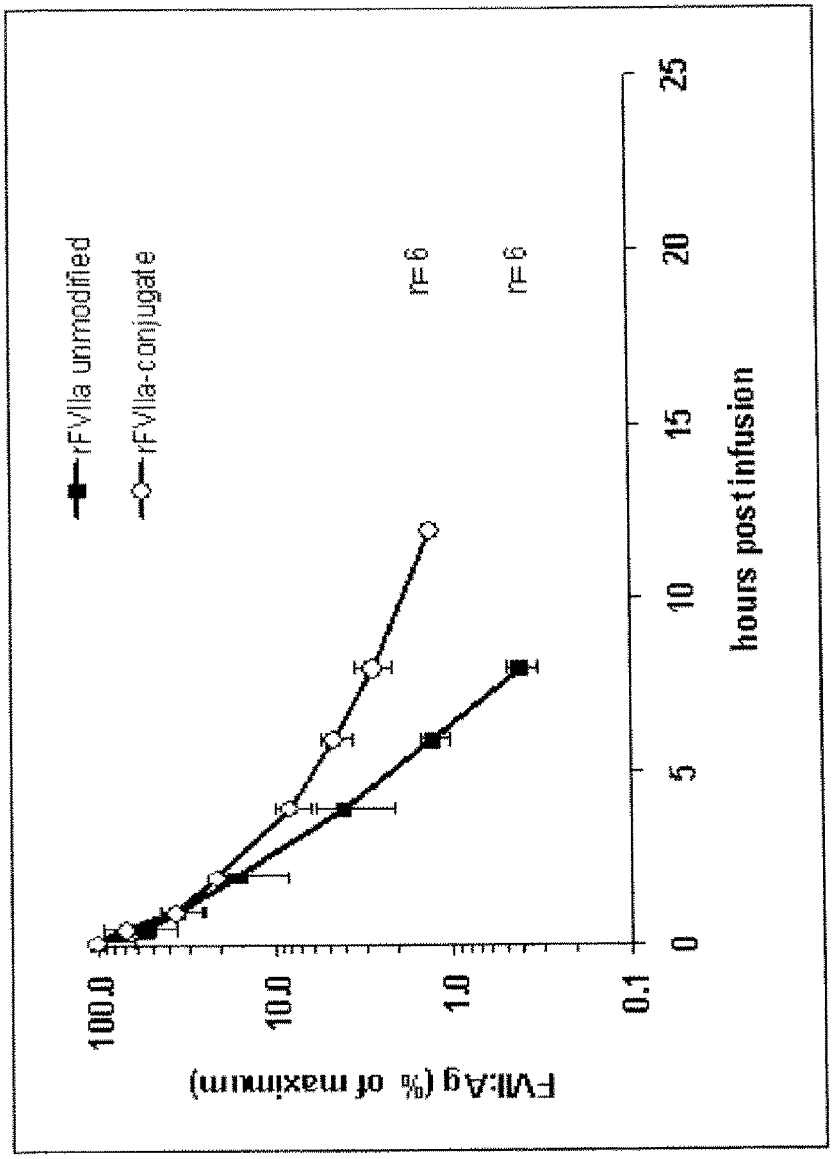
FIG. 3 shows the pharmacokinetics of rFVIIa-PSA-conjugate and unmodified rFVIIa in rats (antigen level)

The pharmocokinetics of FVIIa antigen levels were measured in an additional experiment. Six rats were anaesthetized and rFVIIa-PSA-conjugate (450 μg/kg) in buffer (1.3 g/L glycylglycine, 3 g/L sodium chloride, 30 g/L mannitol, 1.5 g/L $CaCl_2.2H_2O$, 0.1 g/L Tween 80, pH 5.5) was applied by intravenous injection into the tail vein in a volume dose of 10 mL per kg. Unmodified rFVIIa in a dose of 390 μg/kg was used as control in 6 rats. Blood samples were taken from retrobulbary venous plexus, 5 min, 30 min, 1, 2, 4, 6, 8, 12 and 24 h after substance application. Citrate plasma was prepared and frozen for further analysis. FVII antigen levels in plasma were measured with an ELISA (polyclonal anti-human FVII antibody). Half life calculation by linear regression as determined with MS Excel resulted in 1.1 h for native rFVIIa and 3.1 h for the rFVIIa-conjugate. Data for FVII antigen are normalized to the mean plasma level obtained 5 min after application (FIG. 3).

Example 4

N-terminal Polysialylation of FVIIa

The conjugation of CA at the N-terminus of FVIIa was performed at pH 6.0. For this procedure CA from Sigma (Sigma-Aldrich) was used, which was further purified by anion-exchange chromatography on Q-Sepharose FF (GE Healthcare, Munich, Germany). An aqueous solution of purified CA (concentration: 23 mg/mL) containing 0.04 M $NaIO_4$ was stirred for 15 min in the dark at room temperature to oxidize the CA. Subsequently an aliquot of this solution was added to a rFVIIa solution (740 μg/mL) in 0.05 M sodium phosphate buffer, pH 6.0 to give a final concentration of 60 mg activated CA per mg rFVIIa (approx. 150 molar excess). This mixture was stirred for 180 min at room temperature in the dark. $NaCNBH_3$ was added (25 mg/mg rFVIIa) and the mixture was incubated for 24 h at 4° C. in the dark under gentle shaking. Then 2.5 mL of an aqueous 1 M TRIS-solution, pH 7.2 was added per mL of this mixture and stirred in the dark at 4° C. for 60 min to terminate the reaction.

The free reagents were separated from the rFVIIa-CA acid conjugate by ion exchange chromatography using a QHyperD F 50 μm resin (Pall BioSepra, Cergy, France) and a Pharmacia XK-16 column (Pharmacia XK 16; h=14 cm).

Then the CA conjugated protein was eluted with elution buffer (20 mM HEPES/0.5M NaCl, pH 8.0). In a final step the eluate was concentrated by UF/DF using a 10 kD membrane (regenerated cellulose/Millipore) against 20 mM HEPES buffer, pH 7.4 containing 150 mM NaCl. The ion exchange chromatography and the UF/DF step were performed at 4° C.

The enzymatic activity of N-terminal modified rFVIIa-PSA was determined by a clotting assay and by a thrombin generation assay as described in Example 2. The results are summarized in Table 2.

TABLE 2

Specific activity of rFVIIa before and after N-terminal conjugation with PSA

| | FVIIa activity | |
|---|---|---|
| | STF (U/mg protein) | TGA (U/mg protein) |
| unmodified rFVIIa | 52749 | 56814 |
| rFVIIa-PSA - (N terminal) | 25030 | 12564 |

The specific activity of N-terminal conjugated PSA-rFVIIa decreased to approximately 50% as measured by the STF assay, and to 25% by TGA.

Figure 4:
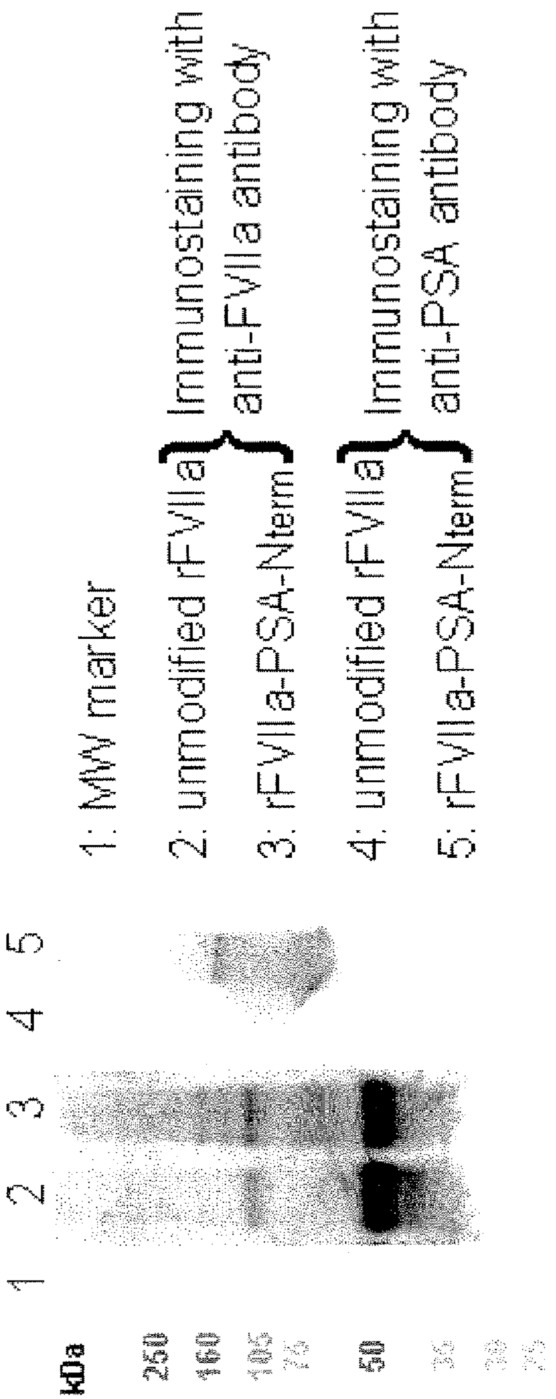
FIG. 4 shows a SDS-PAGE of rFVIIa after N-terminal conjugation with PSA

Modification was visualized by SDS-PAGE performed under non-reducing conditions developed by immunostaining with a polyclonal anti-FVII antibody and with a polyclonal anti-PSA antibody as described in Example 2. Modification resulted in a slight increase of the MW of FVIIa correlating with the bands shown in the anti-PSA-stained immunoblot (FIG. 4).

Example 5

Conjugation of FVIIa with CNBr Activated Synthetic N-acetylneuraminic Acid

RFVIIa was conjugated with N-acetylneuraminic acid as described in U.S. Pat. No. 3,487,890. 350 mg synthetic N-acetylneuraminic acid (Sigma-Aldrich) were dissolved in 10 mL 0.1 M HEPES buffer, pH 9.0. Then 430 mg CNBr (Fluka, Steinhamm, Germany) were added to this solution and the pH was adjusted to 9.5 with 0.5 M NaOH during the activation procedure. After 30 min the pH value was 9.5. Then the pH value was adjusted to 8.4 by addition of 0.1 M HCl. During the whole activation procedure the temperature was controlled by use of an ice bath and kept at 20-25° C. For conjugation of the activated N-acetylneuraminic acid with rFVIIa a solution of rFVIIa (50 mL/0.44 mg rFVIIa/mL) in 50 mM phosphate buffer, pH 7.2 was added and incubated under gentle stirring at room temperature for 30 min. Then 20 mL 0.2 M Tris-buffer were added for termination of the reaction and blocking of free cyanate esters and the mixture was incubated under gentle stirring for 15 min. Finally the solution was concentrated by UF/DF using a 10 kD membrane (regenerated cellulose/Millipore) against 50 mM phosphate buffer, pH 7.2.

Example 6

Conjugation of FVIIa with CNBr Activated Synthetic N-acetylneuraminic Acid Trimer RFVIIa was conjugated to a synthetic N-acetylneuraminic acid trimer obtained from TimTec, LLC (Newark, USA) as described in U.S. Pat. No. 3,487,890 for N-acetylneuraminic acid. 350 mg of the N-acetylneuraminic acid trimer were dissolved in 10 mL 0.1 M HEPES buffer, pH 9.0. Then 430 mg CNBr (Fluka) were added to this solution and the pH was adjusted to 9.5 with 0.5 M NaOH during the activation procedure. After 30 min the pH value was at 9.5. The pH value was adjusted to 8.4 by addition of 0.1 M HCl. During the whole activation procedure the temperature was controlled by use of an ice bath and kept at 20-25° C. Then the conjugation of the activated trimer with FVIIa was performed as described in Example 5.

Example 7

Biochemical Characterization of Mono-SA-FVIIa and Tri-SA-FVIIa

The enzymatic activity of modified rFVIIa-conjugated to N-acetylneuraminic acid (Mono-SA) described in Example 5 or N-acetylneuraminic acid trimer (Tri-SA) described in Example 6 was determined by a clotting assay and by a thrombin generation assay as described in Example 2. The results are summarized in Table 3.

TABLE 3

Specific activity of rFVIIa before and after N-terminal conjugation with PSA

| | FVIIa activity | |
|---|---|---|
| | STF (U/mg protein) | TGA U/mg protein) |
| unmodified rFVIIa | 40579 | 57230 |
| Mono-SA-rFVIIa | 6064 | 21784 |
| Tri-SA-rFVIIa | 1743 | 4131 |

The specific activity of the oligo-PSA conjugated rFVIIa decreased as measured by the STF assay, but the mono-SA-rFVIIa retained about 50% of its FVIII-bypassing activity, measured by TGA.

Figure 5:
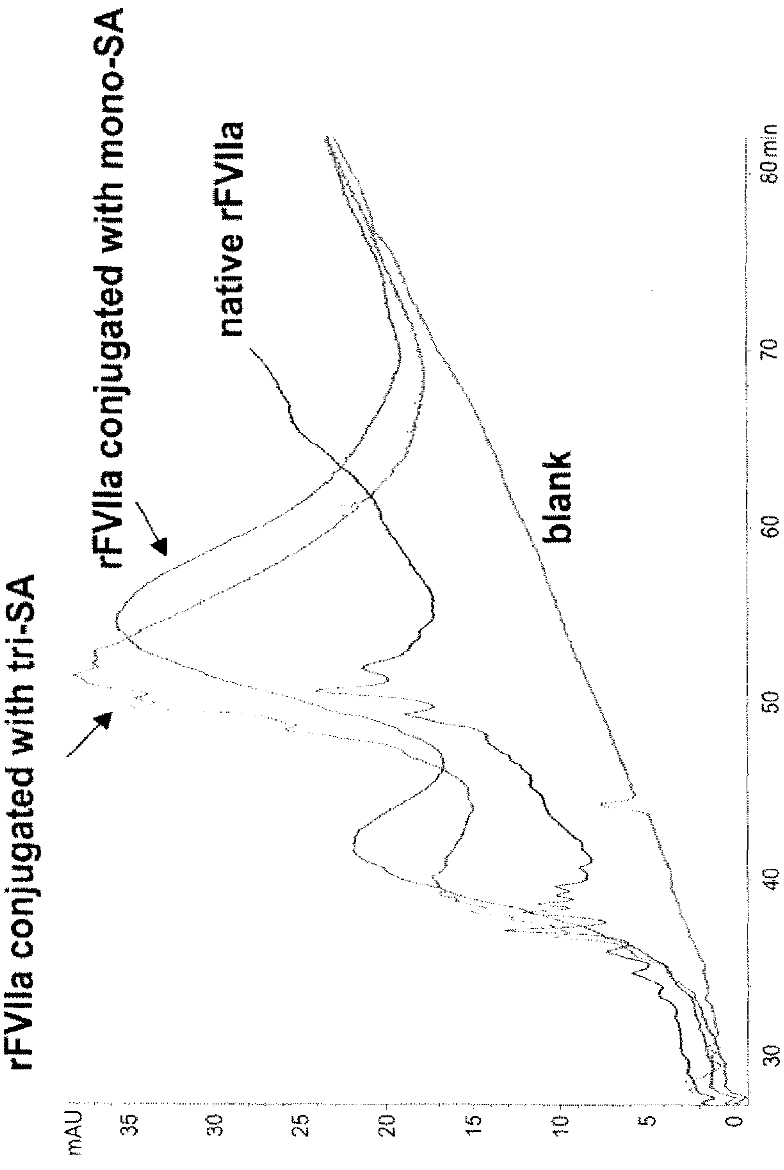
FIG. 5 shows a capillary electrophoresis of mono-SA rFVIIa and Tri-SA-rFVIIa FIGS. 6A and B show the pharmacokinetics of rFVIIa-PSA-conjugates and unmodified rFVIIa in rats, A: mono-SA-rFVIIa, B: tri-SA-rFVIIa

In addition Mono-SA rFVIIa and Tri-SA-rFVIIa were investigated by capillary electrophoresis (CE) as described by Klausen and Kornfelt (J Chromatogr A. 1995; 718:195-202). The results are illustrated in FIG. 5. A clear shift to higher retention times of the Mono-SA rFVIIa and Tri-SA-rFVIIa due to additional negative charges in comparison to the native rFVIIa is indicated.

Example 8

Pharmacokinetics of rFVIIa-Mono SA and rFVIIa-Tri SA Conjugate in Rats

Figure 6A:
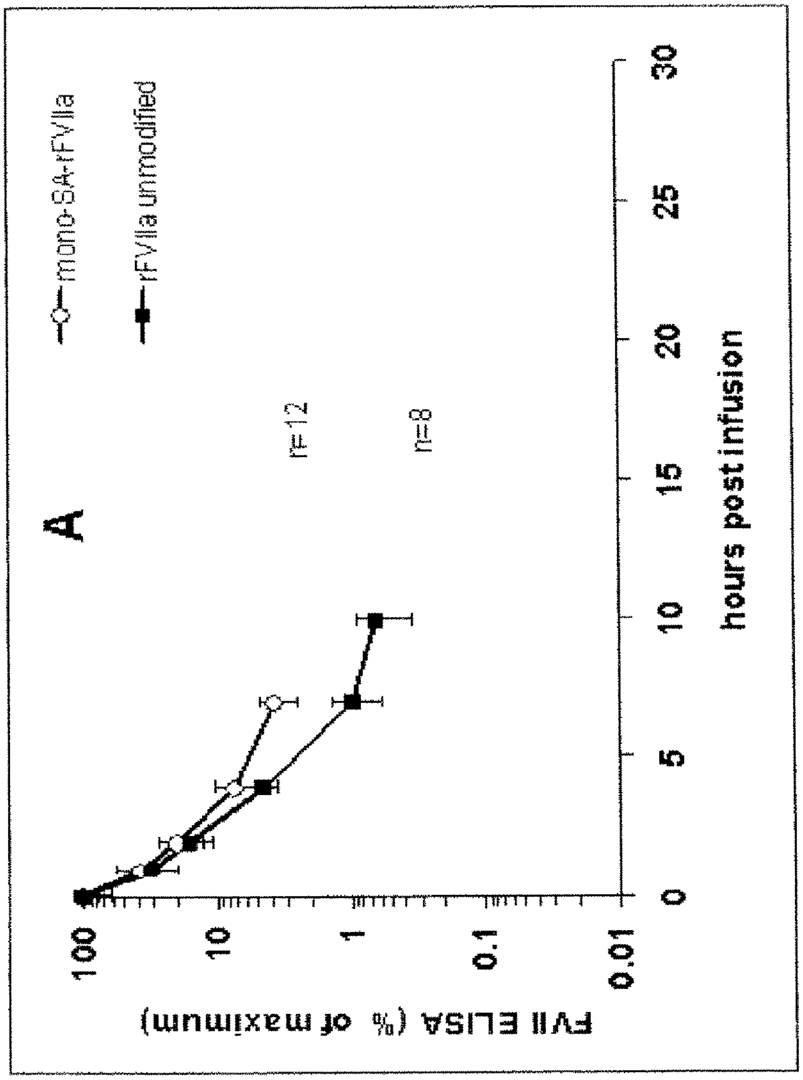
Figure 6B:
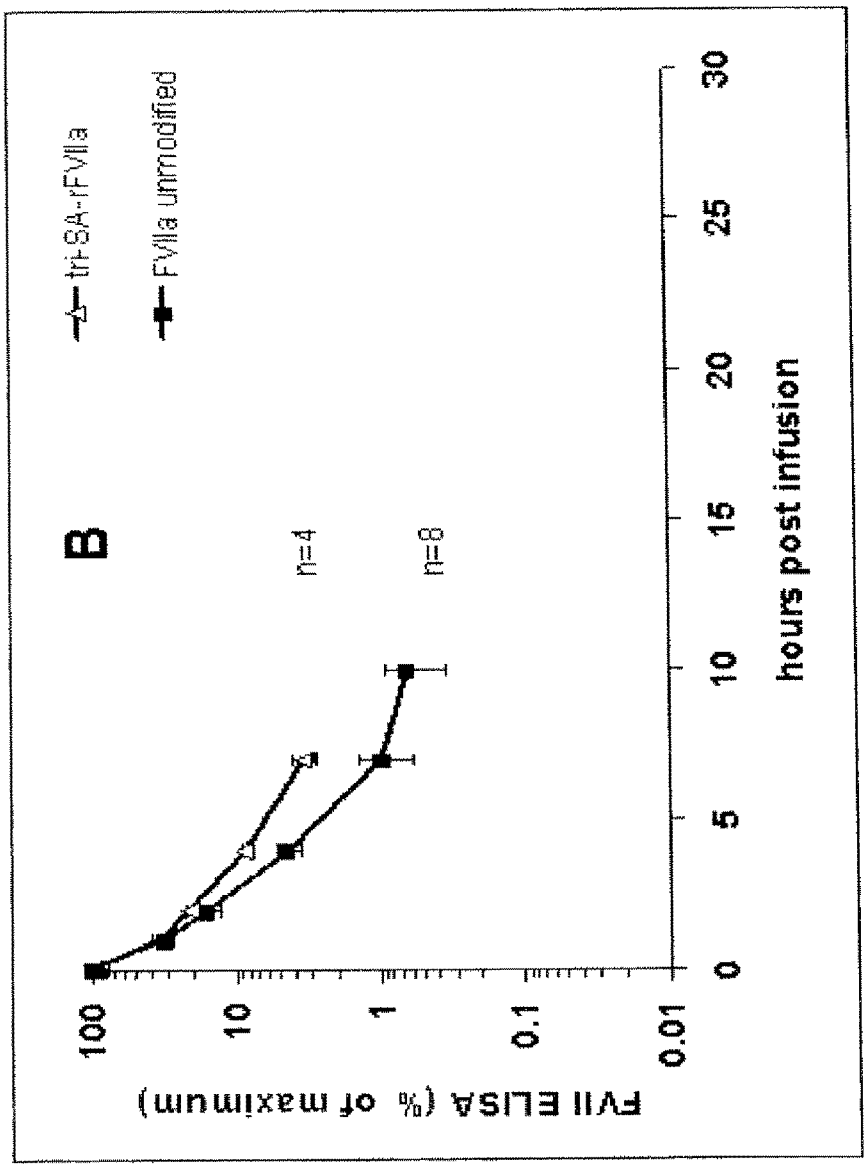

Twelve rats were anaesthetized and rFVIIa-mono SA-conjugate (400 μg protein/kg) in buffer (1.3 g/L glycylglycine, 3 g/L sodium chloride, 30 g/L mannitol, 1.5 g/L $CaCl_2.2H_2O$, 0.1 g/L Tween 80, pH 5.5) was applied by intravenous injection into the tail vein in a volume dose of 10 mL per kg. Four rats were treated with rFVIIa-tri SA-conjugate (400 μg protein/kg). Unmodified rFVIIa in a dose of 400 μg protein/kg was used as control in 8 normal rats. Blood samples were taken from retrobulbary venous plexus, 5 min, 30 min, 1, 2, 4, 7, 10 and 22 h after substance application, citrate plasma was prepared and frozen for further analysis. FVII antigen levels in plasma were measured with an ELISA (polyclonal anti-human FVII antibody). Data were normalized relative to the concentration, found in plasma 5 min after application. 7 h after application, the plasma levels for rFVIIa-mono-SA and tri-SA-rFVIIa were higher than for the native rFVIIa control. The results are illustrated in FIG. 6A (rFVIIa-mono SA) and FIG. 6B (rFVIIa-tri SA).

Example 9

Coupling of N-acetylneuraminic Acid Trimer to rFVIIa by Reductive Amination

The conjugation of rFVIIa with N-acetylneuraminic acid trimer by reductive amination was carried out as described by Biessen et al. (Biochem J 1994; 299:291-6). 350 mg N-acetylneuraminic acid trimer (TimTec) were dissolved in 10 mL 0.1 M HEPES buffer, pH 7.0 and added to 32 mL of a solution of recombinant FVIIa in 20 mM HEPES, 70 mm NaCl, pH 7.4 (0.3 mg/mL). Then $NaCNBH_3$ was added to give a final concentration of 50 mg/mL and the pH was corrected to pH 7.0 by addition of 0.1 M HCl. The mixture was incubated at 37° C. under gentle stirring for 48 h. The solution was concentrated by UF/DF using a 10 kD membrane (regenerated cellulose/Millipore) against 20 mM Hepes buffer, 150 mM NaCl, pH 7.4.

Figure 7:
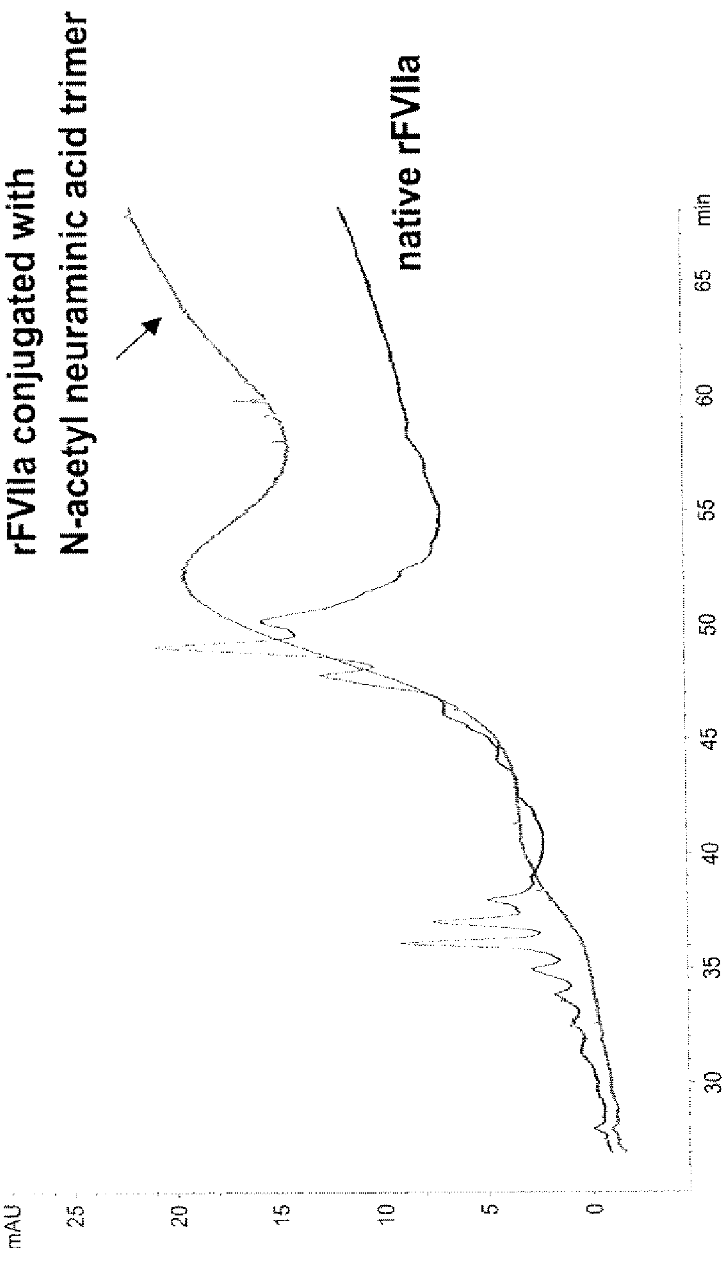
FIG. 7 shows a capillary electrophoresis of N-acetylneuraminic acid trimer The present invention will be further illustrated in the following examples, without any limitation thereto.

The conjugation of the N-acetylneuraminic acid trimer to the rFVIIa was shown by CE performed according to Klausen and Kornfelt (J Chromatogr A. 1995, 718:195-202,). The results are indicated in FIG. 7. A clear shift of the derivative to higher retention times in comparison to the native rFVIIa is indicated.

Example 10

Purification and Derivatization of Colominic Acid

CA was purified by of anion-exchange chromatography on Q-Sepharose FF as described in WO0601616A1. Five g CA were dissolved in 50 mL 10 mM Triethanolamine buffer, pH 7.4 containing 25 mM NaCl (=starting buffer). This solution was applied onto a Pharmacia XK50 column filled with Q-Sepharose FF (GE Healthcare), which was equilibrated with starting buffer. Then the column was washed with 8 column volumes (CV) starting buffer and the bound CA was eluted stepwise with 3CV 200 mM NaCl, 350 mM NaCl and 500 mM NaCl in starting buffer. The fraction eluted with 350 mM NaCl showed a molecular weight of 20 kDa as indicated by SDS gel electrophoresis. This fraction was concentrated by ultrafiltration using a 5 kD membrane made of regenerated cellulose (Millipore) and subsequently diafiltrated against 50 mM phosphate buffer, pH 7.2. Then the CA was oxidized with $NaIO_4$ as described in Example 1 and a terminal primary amino group was introduced by reductive amination as described in WO05016973A1. For reductive amination 11 mL of a 2 M $NH_4Cl$-solution were added to 20 mL of a solution containing 58 mg oxidized PSA/ml in 50 mM phosphate buffer, pH 7.2. Then a solution of 5M $NaCNBH_3$ in 1M NaOH was added to give a final concentration of 75 mM. The reaction was performed for 5 d at room temperature at pH 8.0. Then the mixture was dialyzed against a $(NH_4)_2CO_3$ solution (50 mg/L) containing 10 mM NaCl and subsequently against 50 mM phosphate buffer, pH 8.0, containing 5 mM EDTA. Then a sulfhydryl group was introduced by reaction of the terminal primary amino group with 2-iminothiolane (Traut's reagent/Pierce). The reaction was carried out in 50 mM phosphate buffer, pH 8.0, containing 5 mM EDTA with 20 fold molar excess of reagent for 1 h at room temperature. Finally the PSA solution containing a terminal free SH-group was subjected to ultrafiltration/diafiltration using a membrane with a cut-off of 5 kD and made of regenerated cellulose (Millipore).

Example 11

Coupling of PSA to rFVIIa by use of a Heterobifunctional Cross-linker

PSA (Sigma-Aldrich) was purified by anion-exchange chromatography on Q-Sepharose FF (GE-Healthcare) and a terminal sulfhydryl-group was introduced by chemical modification to form PSA-SH as described in Example 10. For coupling of PSA-SH to rFVIIa the heterobifunctional, water soluble cross-linker Sulfo-EMCS ((N-ε-Maleimidocaproyloxy)sulfosuccinimide ester/Pierce) was used, containing two reactive groups: a maleimide group for conjugation to SH-groups and a sulfo-NHS-ester group for conjugation to free amino groups. To 2 mL of a rFVIIa solution (1.6 mg/mL) in 20 mM HEPES buffer, pH 7.4 containing 150 mM NaCl Sulfo-EMCS was added to give a final concentration of 0.07 mg cross linker/mg protein). The reaction was carried out for 30 min at room temperature. Subsequently 130 mg PSA-SH (100 fold excess) prepared according to Example 10 was added and the coupling reaction of the intermediate linker/rFVIIa complex to the PSA-SH was performed for additional 2 h at room temperature. Then the mixture was purified by HIC chromatography on Butyl-Sepharose (GE-Healthcare). A 5 M NaCl solution was added to the mixture to give a final concentration of 3 M NaCl. Then this mixture was applied to the column filled with Butyl-Sepharose (GE-Healthcare) and the elution of the rFVIIa-PSA conjugate was carried out with 50 mM HEPES-buffer, pH 7.4, containing 6.7 mM $CaCl_2$. After elution of the conjugate the pH was adjusted to pH 6.9.

Example 12

Conjugation of PSA-hydrazide to the Carbohydrate Moiety of rFVIIa

For conjugation of PSA to the carbohydrate moiety of rFVIIa a solution of rFVIIa in 20 mM HEPES buffer, pH 6.0 (1.6 mg/mL) is prepared. To 9 volumes of this solution 1 volume of a 5 mM $NaIO_4$-solution is added and gently mixed. The oxidation reaction is carried out for 1 h at 4° C. in the dark to generate free aldehyde groups. Then sodium bisulfite (final concentration 5 mM) is added to stop the reaction. Subsequently PSA-hydrazide (WO0606168A2) is added (final concentration 10 mM) and the coupling reaction to the aldehyde groups is performed for 1 h at room temperature. Then the PSA-rFVIIa conjugate is purified by anion-exchange chromatography on QHyperD (Pall BioSepra) as described in Example 1.

The invention claimed is:

1. A chemically-modified proteinaceous construct comprising, (a) an activated factor VII (FVIIa) molecule which is plasmatic FVIIa or recombinant FVIIa (rFVIIa); and (b) at least one physiologically acceptable carbohydrate moiety comprising 1-4 sialic acid units bound to said FVIIa molecule;

wherein the in vivo half-life of said construct is prolonged in the blood of a mammal as compared to the in vivo half-life of a FVIIa molecule that is not chemically-modified.

2. The chemically-modified proteinaceous construct of claim 1 wherein the in vivo half-life of said construct is increased by at least a factor of about two as compared to the in vivo half-life of a FVIIa molecule that is not chemically-modified.

3. The chemically-modified proteinaceous construct of claim 1 wherein the in vivo half-life of said construct is increased by at least a factor of about three as compared to the in vivo half-life of a FVIIa molecule that is not chemically-modified.

4. The chemically-modified proteinaceous construct of claim 1, wherein the physiologically acceptable carbohydrate moiety is directly covalently linked to at least one amino acid residue of said FVIIa molecule.

5. The chemically-modified proteinaceous construct of claim 1, wherein the physiologically acceptable carbohydrate moiety is non-covalently linked to at least one amino acid residue of said FVIIa molecule.

6. The chemically-modified proteinaceous construct of claim 1, wherein said physiologically acceptable carbohydrate moiety is a polysialic acid.

7. A pharmaceutical composition comprising an effective amount of the chemically-modified proteinaceous construct of claim 1, and one or more compounds selected from the group consisting of a pharmaceutically acceptable carrier, diluent, salt, buffer, and excipient.

8. A method of controlling bleeding in a mammal having a bleeding disorder associated with functional defects or deficiencies of at least one of FVIIa, factor VIII (FVIII) and factor IX (FIX), said method comprising administering the chemically-modified proteinaceous construct of claim 1.

9. A method of controlling bleeding in a mammal during surgery or trauma, said method comprising administering the chemically-modified proteinaceous construct of claim 1.

10. A kit comprising an effective amount of the chemically-modified proteinaceous construct of claim 1, packaged in a container, said kit optionally containing a second therapeutic agent, and further comprising a label attached to or packaged with the container, the label describing the contents of the container and providing indications and/or instructions regarding use of the contents of the container for controlling bleeding in a mammal.

11. The kit of claim 10 wherein the container is a vial or bottle or prefilled syringe.

* * * * *